United States Patent
Nigg et al.

(10) Patent No.: US 11,359,830 B2
(45) Date of Patent: Jun. 14, 2022

(54) SENSOR DEVICE AND SECURED WIRELESS COMMUNICATION PROTOCOL FOR AIR QUALITY SENSOR DEVICES

(71) Applicant: Integrated Energy Services Corporation, New York, NY (US)

(72) Inventors: Brock L. Nigg, Darien, CT (US); Steve Schlanger, Flagstaff, AZ (US); Frank Ableson, Stanhope, NJ (US)

(73) Assignee: Integrated Energy Services Corporation, New York, NY (US)

( * ) Notice: Subject to any disclaimer, the term of this patent is extended or adjusted under 35 U.S.C. 154(b) by 0 days.

(21) Appl. No.: 17/015,918

(22) Filed: Sep. 9, 2020

(65) Prior Publication Data

US 2021/0076328 A1 Mar. 11, 2021

Related U.S. Application Data

(60) Provisional application No. 62/898,248, filed on Sep. 10, 2019.

(51) Int. Cl.
*F24F 11/46* (2018.01)
*F24F 11/58* (2018.01)
(Continued)

(52) U.S. Cl.
CPC .............. *F24F 11/46* (2018.01); *F24F 11/39* (2018.01); *F24F 11/47* (2018.01); *F24F 11/52* (2018.01);
(Continued)

(58) Field of Classification Search
CPC .. F24F 11/39; F24F 11/46; F24F 11/47; F24F 11/52; F24F 11/58; F24F 11/63;
(Continued)

(56) References Cited

U.S. PATENT DOCUMENTS

| 7,599,815 B2 | 10/2009 | Reichel et al. |
| 8,428,909 B2 | 4/2013 | Collins |

(Continued)

FOREIGN PATENT DOCUMENTS

| CN | 109028510 A | 12/2018 |
| RU | 2439442 C1 | 1/2012 |

OTHER PUBLICATIONS

Hagan et. al., "Calibration and Assessment of Electrochemical Air Quality Sensors by Co-Location with Regulatory-Grade Instruments", Atmospheric Measurement Techniques, 2018, pp. 315-328.
(Continued)

*Primary Examiner* — Francis C Gray
(74) *Attorney, Agent, or Firm* — M&B IP Analysts, LLC

(57) ABSTRACT

A system and method for secured and power-efficient communication between a sensor device and a control device operable in an air-quality system. The method includes receiving, during a first time period, a wake-up signal, wherein the wake-up signal includes at least a packet number; sending, during a second time period, an acknowledgment (ACK) signal, wherein an ACK signal is sent in reference to a synchronized time slot and a packet number; sending, during a third time period, at least sensor reading data of at least one air quality detector, wherein the sensor reading data is encrypted using at least an encryption key; receiving, during a fourth time period, a sleep signal; and entering into a sleep mode upon receipt of the sleep signal.

20 Claims, 6 Drawing Sheets

(51) Int. Cl.

| | | |
|---|---|---|
| *F24F 11/52* | (2018.01) | |
| *F24F 11/63* | (2018.01) | |
| *G01N 33/00* | (2006.01) | |
| *H04W 52/02* | (2009.01) | |
| *F24F 11/39* | (2018.01) | |
| *F24F 11/47* | (2018.01) | |
| *G08C 17/02* | (2006.01) | |
| *F24F 110/50* | (2018.01) | |
| *F24F 110/20* | (2018.01) | |
| *F24F 140/60* | (2018.01) | |
| *F24F 110/70* | (2018.01) | |
| *F24F 110/74* | (2018.01) | |
| *F24F 110/40* | (2018.01) | |
| *F24F 110/66* | (2018.01) | |
| *F24F 110/10* | (2018.01) | |

(52) U.S. Cl.
CPC .............. *F24F 11/58* (2018.01); *F24F 11/63* (2018.01); *G01N 33/0006* (2013.01); *G01N 33/0073* (2013.01); *G01N 33/0075* (2013.01); *G08C 17/02* (2013.01); *H04W 52/0206* (2013.01); *H04W 52/0235* (2013.01); *F24F 2110/10* (2018.01); *F24F 2110/20* (2018.01); *F24F 2110/40* (2018.01); *F24F 2110/50* (2018.01); *F24F 2110/66* (2018.01); *F24F 2110/70* (2018.01); *F24F 2110/74* (2018.01); *F24F 2140/60* (2018.01); *G08C 2201/12* (2013.01); *G08C 2201/40* (2013.01)

(58) Field of Classification Search
CPC ............... F24F 2110/10; F24F 2110/20; F24F 2110/40; F24F 2110/50; F24F 2110/66; F24F 2110/70; F24F 2110/74; F24F 2140/60; G01N 33/0006; G01N 33/0073; G01N 33/0075; H04W 52/0206; H04W 52/0235
See application file for complete search history.

(56) References Cited

U.S. PATENT DOCUMENTS

| | | | |
|---|---|---|---|
| 8,682,937 | B2 | 3/2014 | Ludwig |
| 9,756,403 | B2 | 9/2017 | Proud |
| 2007/0242688 | A1 | 10/2007 | McFarland |
| 2009/0012738 | A1 | 1/2009 | Hart et al. |
| 2010/0081411 | A1 | 4/2010 | Montenero |
| 2010/0177750 | A1* | 7/2010 | Essinger ................. H04L 67/12 370/338 |
| 2011/0074552 | A1* | 3/2011 | Norair .................. G06K 7/0008 340/10.1 |
| 2012/0303164 | A1* | 11/2012 | Smith ..................... H04L 67/12 700/276 |
| 2013/0298642 | A1 | 11/2013 | Gillette, II |
| 2014/0053586 | A1 | 2/2014 | Poecher et al. |
| 2014/0247140 | A1* | 9/2014 | Proud ..................... H04W 4/70 340/870.02 |
| 2015/0096352 | A1* | 4/2015 | Peterson ................ G08B 21/12 73/31.02 |
| 2016/0116181 | A1 | 4/2016 | Aultman et al. |
| 2016/0360300 | A1* | 12/2016 | Proud .................... G08C 17/02 |
| 2018/0120279 | A1* | 5/2018 | Yi ...................... G01N 33/0073 |

OTHER PUBLICATIONS

International Search Report and Written Opinion of International Searching Authority for PCT/US2020/048472, ISA/RU, Moscow, Russia, dated Nov. 19, 2020.
International Search Report and Written Opinion of International Searching Authority for PCT/US2020/049934, ISA/RU, Moscow, Russia, dated Nov. 11, 2020.
International Search Report and Written Opinion of International Searching Authority for PCT/US2020/049937, ISA/RU, Moscow, Russia, dated Nov. 26, 2020.
International Search Report and Written Opinion of International Searching Authority for PCT/US2020/050198, ISA/RU, Moscow, Russia, dated Nov. 13, 2020.
Vaquerizo-Hdez et. al., "A Low Power Consumption Algorithm for Efficient Energy Consumption in ZigBee Motes", Intelligent Systems Group, Computer Engineering Department, Universidad de Alcala; Sensors: MDPI, Aug. 19, 2017.

* cited by examiner

SENSOR DEVICE AND SECURED WIRELESS COMMUNICATION PROTOCOL FOR AIR QUALITY SENSOR DEVICES

CROSS-REFERENCE TO RELATED APPLICATIONS

This application claims the benefit of U.S. Provisional Application No. 62/898,248 filed on Sep. 10, 2019, the contents of which are hereby incorporated by reference.

TECHNICAL FIELD

The present disclosure relates generally to air quality assurance and energy management and, more particularly, to sensor devices and secured wireless communication protocol for air quality sensor devices.

BACKGROUND

While certain improvements in building materials, construction techniques, and electronic systems provide for improved efficiency in operations of a building, energy costs remain among a building operator's greatest expense. Energy costs, such as those costs arising from heating or cooling a building, may vary greatly based on factors such as resident or tenant environmental preferences, demand-based energy pricing, environmental conditions, and the like. Further, building operators may wish to provide for the comfort of tenants and residents, in addition to cost-optimization, creating a complex balance of energy costs and building requirements, a balance which legacy systems may be ill-equipped to resolve.

Legacy building management systems may provide for the collection of data relating to building environmental conditions. Further, such legacy systems may include features providing for control of building conditions using devices such as thermostat-linked heating and cooling systems, remote shutoffs for conduits, and the like. While such legacy systems may provide for environmental control and data collection, legacy means may be ill-suited to high-volume data processing and may lack certain connectivity features useful in reducing operator workload and maintenance. In addition, legacy building management system data collection devices and systems may be limited to those sensing and data collection devices installed, configured, and supported. Such limitations may hinder a building operator's ability to integrate modern sensing and data collection capabilities with legacy building management systems.

In addition to the inefficiencies of legacy systems in managing high-volume building data, such systems may fail to provide certain modern functionalities necessary for efficient building environmental system management. Legacy systems may lack cloud-processing systems which provide for collection and analysis of large volumes of building data. Further, legacy systems may lack the interconnectivity required to collect energy market and grid data and to respond to such data automatically. In addition, legacy systems may require manual calibration and re-calibration of sensor and regulator devices, where manual calibration and re-calibration may require a prohibitively large outlay of time and effort on the part of building management and maintenance teams.

Further, legacy systems may fail to provide for management of building wellness controls. Building wellness controls include those controls concerning health and wellness parameters of building management, such as air filter status, air quality, drinking water contamination, and the like, as opposed to comfort controls which may be directed to provision of comfortable conditions for building occupants, such as controls directed to air temperatures. Further, legacy systems may require various trade-offs between wellness, comfort, and energy efficiency in order to reach various building management goals. As a result, legacy systems may lack the capacity to provide optimized wellness, comfort, and energy solutions, requiring intensive manual adjustment of wellness, comfort, and energy parameters to reach desired building control states.

In addition to legacy building management systems, certain smaller-scale comfort and energy management systems may provide similar functionalities in smaller-scope applications, such as homes, small offices, and the like. Examples of smaller-scale comfort and energy management systems include the Nest® home management system by Google®. While smaller-scale systems provide for certain energy and comfort control functionalities, such systems lack the scope of application required to provide centrally-managed control of wellness, air quality, comfort, and energy needs for larger buildings such as office towers, retail stores, and the like, as such buildings may include large numbers of management devices, complex connectivity architectures, predefined communication protocols, and the like. Further, smaller-scale systems may be primarily directed to management of comfort and energy parameters, to the exclusion of integrated safety and wellness controls. As a result, smaller-scale management systems may fail to provide functionalities and scopes of application required for use in large-scale building systems management applications.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein also include a sensor device operable in an air-quality control system. The sensor device comprises a radio circuit configured to wirelessly communicate with a control device, wherein the communication is facilitated using an air-quality communication protocol; an array of air-quality detectors; a processing circuitry; and a memory, the memory containing instructions that, when executed by the processing circuitry, configure the sensor device to: receive, during a first time period, a wake-up signal, wherein the wake-up signal includes at least a packet number; send, during a second time period, an acknowledgment (ACK) signal, wherein an ACK signal is sent in reference to a synchronized time slot and a packet number; send, during a third time period, at least sensor reading data of least one air quality detector, wherein the sensor reading data is encrypted using at least an encryption key stored in the memory; receive, during a fourth time period, a sleep signal; and enter into a sleep mode upon receipt of the sleep signal.

Certain embodiments disclosed herein include a method for secured and power-efficient communication between a sensor device and a control device operable in an air-quality system. The method comprises receiving, during a first time period, a wake-up signal, wherein the wake-up signal includes at least a packet number; sending, during a second time period, an acknowledgment (ACK) signal, wherein an ACK signal is sent in reference to a synchronized time slot and a packet number; sending, during a third time period, at least sensor reading data of at least one air quality detector, wherein the sensor reading data is encrypted using at least an encryption key; receiving, during a fourth time period, a sleep signal; and entering into a sleep mode upon receipt of the sleep signal.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
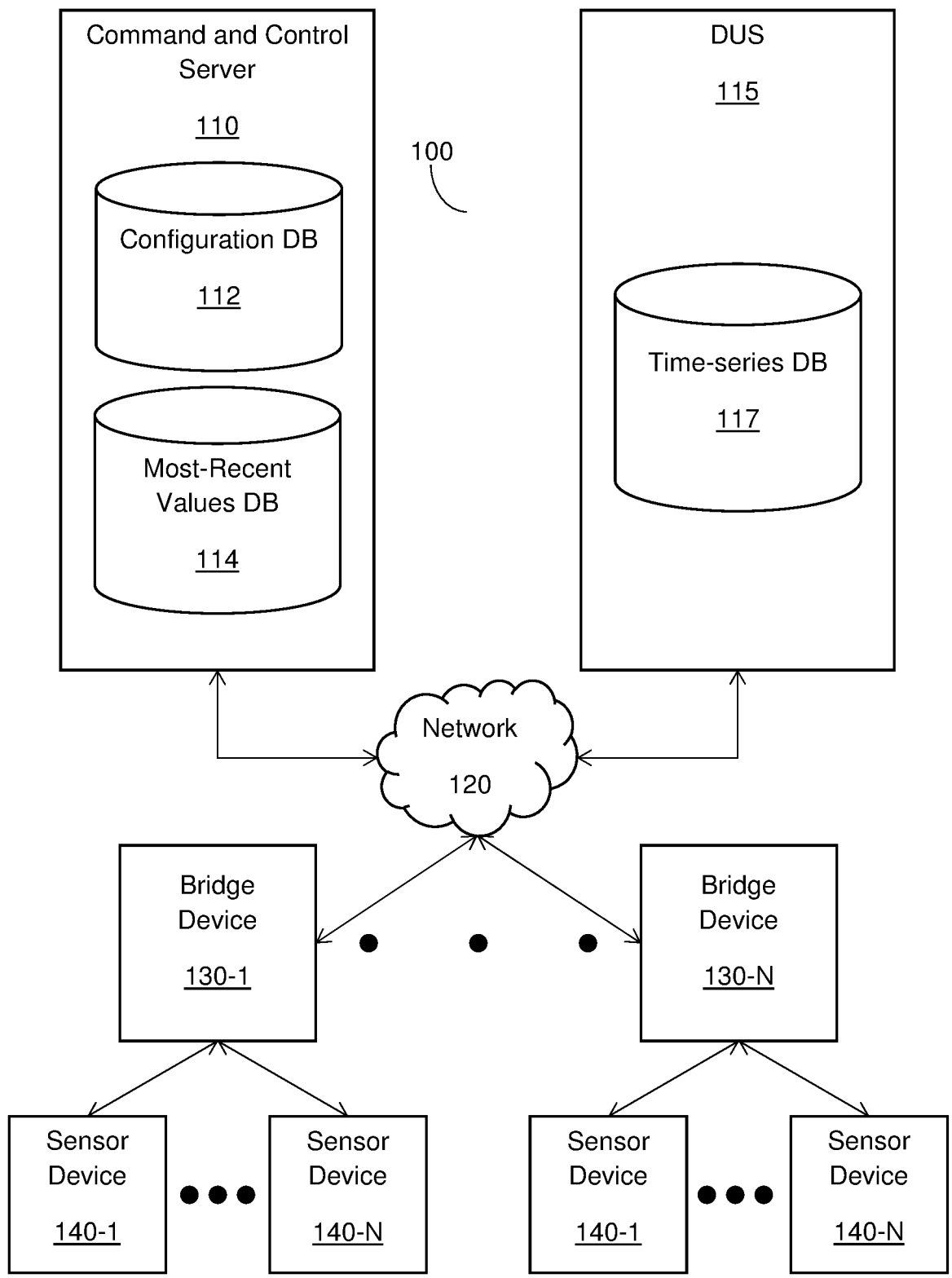
FIG. 1 is a network diagram utilized to describe a system for management of building air quality assurance, according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

FIG. 1 is an example network system 100 depicting the various embodiments for management of building air quality assurance, according to an embodiment. A network system 100 may include one or more components such as, as examples and without limitation, a command and control server (CCS) 110, a data upload server (DUS) 115, a network 120, one or more bridge devices 130-1 through 130-N (hereinafter, "bridge device" 130 or "bridge devices" 130), as well as one or more sensor devices 140-1 through 140-N (hereinafter, "sensors" 140 or "sensor" 140). In an embodiment, a bridge device 130 is a building air quality assurance device.

The CCS 110 provides for cloud-level administration of one or more bridge device 130. The CCS 110 may include a configuration database 112, a most-recent values database 114, and the like, as well as any combination thereof. The CCS 110 may be configured to communicate with one or more components of the network system 100 via the network 120, according to the means described hereinbelow. Further, the CCS 110 may be configured to execute one or more of the methods or processes described hereinbelow, including execution of various data processing methods and routines. The CCS 110 may include various processing, memory, and networking components, and the like, allowing the CCS 110 to execute instructions and provide data processing. The CCS 110 may be implemented as physical hardware, as software virtualizing physical hardware, or as a combination of physical and virtualized components. In an embodiment, the CCS 110 may be configured to operate as a data upload server (DUS) 115, as described hereinbelow.

The most recent values database 114 provides storage for register data, as may be collected according to the processes described hereinbelow, organized by order of receipt. Registers may include data features describing, variously, device and component operating systems, device-specific data features, user-defined features, and the like. Register data may include data relating to the operating system or systems of various components of a network system 100.

In addition, register data may include data relating to the operation of various components of a network system, describing component-specific data features, such as, as an example and without limitation, the firmware version of a specific sensor. Further, register data may include user register data, where user register data is data relevant to a user's custom purpose. As an example, user register data may include custom-generated instruction sets for personalizing sensor device data output formats.

The configuration database 112 provides storage for system configuration instructions and collected data. Data which may be stored in the configuration database 112 includes, as examples and without limitation, sensor calibration data, building management system interface data, updated code images, various factory commands, DUS assignments, market and environmental data, register updates, device-specific commands, other, like, data, and any combination thereof.

The data upload server (DUS) 115, is a cloud-level server providing for collection and storage of data from one or more bridge devices 130, sensor devices 140, connected building management systems (not shown), and the like, as well as any combination thereof. The DUS 115 may be a resident server, located and operated on-location where the one or more bridge devices 130 and sensor devices 140 are deployed. Further, the DUS 115 may be a hosted server, located off-site and, in an embodiment, hosted by a platform configured to provide cloud computing, storage, and other, like, services, including, as examples and without limitation, Amazon® Web Services, Microsoft® Azure, and other, like, platforms. The DUS 115 may include one or more storage or memory components, such as the time series database 117, and the like. The time series database 117 may be configured to store data received or collected according to the methods described hereinbelow, as well as other, like, methods.

Data stored in the DUS 115, including data stored in the time series database 117, may be encrypted, unencrypted, or partially-encrypted. Further, stored data may be compressed to various degrees and may be stored to one or more physical partitions or other, like, separated storage allocations. The DUS 115, and any sub-component thereof, may be implemented as physical hardware, as software virtualizing physical hardware, or as a combination of physical and virtualized components. Further, the DUS 115 may be interconnected with the various components of the network system 100, via the network 120, according to the various means described hereinbelow.

The network 120 provides interconnectivity between the various components of the network system 100. The network 120 may be, but is not limited to, a wireless, cellular, or wired network, a local area network (LAN), a wide area network (WAN), a metro area network (MAN), the Internet, the worldwide web (WWW), similar networks, and any combination thereof. The network may be a full-physical network, including exclusively physical hardware, a fully-virtual network, including only simulated or otherwise virtualized components, or a hybrid physical-virtual network, including both physical and virtualized components. Further, the network 120 may be configured to encrypt data, both at rest and in motion, and to transmit encrypted, unencrypted, or partially-encrypted data.

The bridge devices 130 are devices configured to serve as intermediaries between the sensor devices 140 and the various components of the network system 100. The bridge devices 130 may be configured to, as examples and without limitation, collect data from the various sensor devices 140, to upload or push instructions to the various sensor devices 140, to upload or push collected data to the various components of the network system 100, to collect, from the various components of the network system 100, various instructions, to collect data, independent of the various sensor devices 140, to execute instructions, and the like, as well as any combination thereof.

The bridge devices 130 may be configured to connect with the various components of the network system 100 via the network 120, according to the means described hereinabove. Further, the bridge devices 130 may be configured to connect with the various sensor devices 140 via wired or wireless means, or any combination thereof, such as those described hereinabove, via those protocols described with respect to the network 120, as well as other, like, protocols, or any combination thereof. In addition, the bridge devices 130 may be configured to encrypt data, both at rest and in motion, and to transmit data with varying degrees of encryption.

According to the disclosed embodiments, the bridge devices 130 may be configured to execute instructions, and process data, for local management of building air quality assurance devices. Local building air quality assurance devices may be, sensor devices 140, other, like, devices, and any combination thereof, some or all of which may be configured to provide functionality pertaining to building air quality. The bridge devices 130 may be configured to execute instructions and process data relevant to the various components of the system via connections to the various devices according to various pre-defined communication protocols, patterns, exchange systems, and the like, including via the network 120, as described hereinabove.

The sensor devices 140 are devices configured to provide for collection of data pertinent to building air quality. The sensor devices 140 may be include one or more sensors such as, as examples and without limitation, thermometers and gas detection and measurement sensors, hygrometers, and the like, as well as any combination thereof. Further, sensor devices 140 may be configured to collect data and to transmit collected data to the various components of the network system 100 via the bridge devices 130, to execute instructions received, via the bridge devices 130, from the various components of the network system 100, to execute other, like, functions, as well as any combination thereof. The sensor devices 140 may be configured to connect with the bridge devices 130 via those means described hereinabove. The sensor device 140 may be configured to execute one or more of the processes described herein. A hardware configuration of a sensor device 140, and an associated microcontroller, are described, respectively, with respect to FIGS. 2a and 2b, below. In an embodiment, the sensor devices 140 may be configured to connect directly with the network 120, via those means described herein, without connection to a bridge device 130.

Figure 2A:
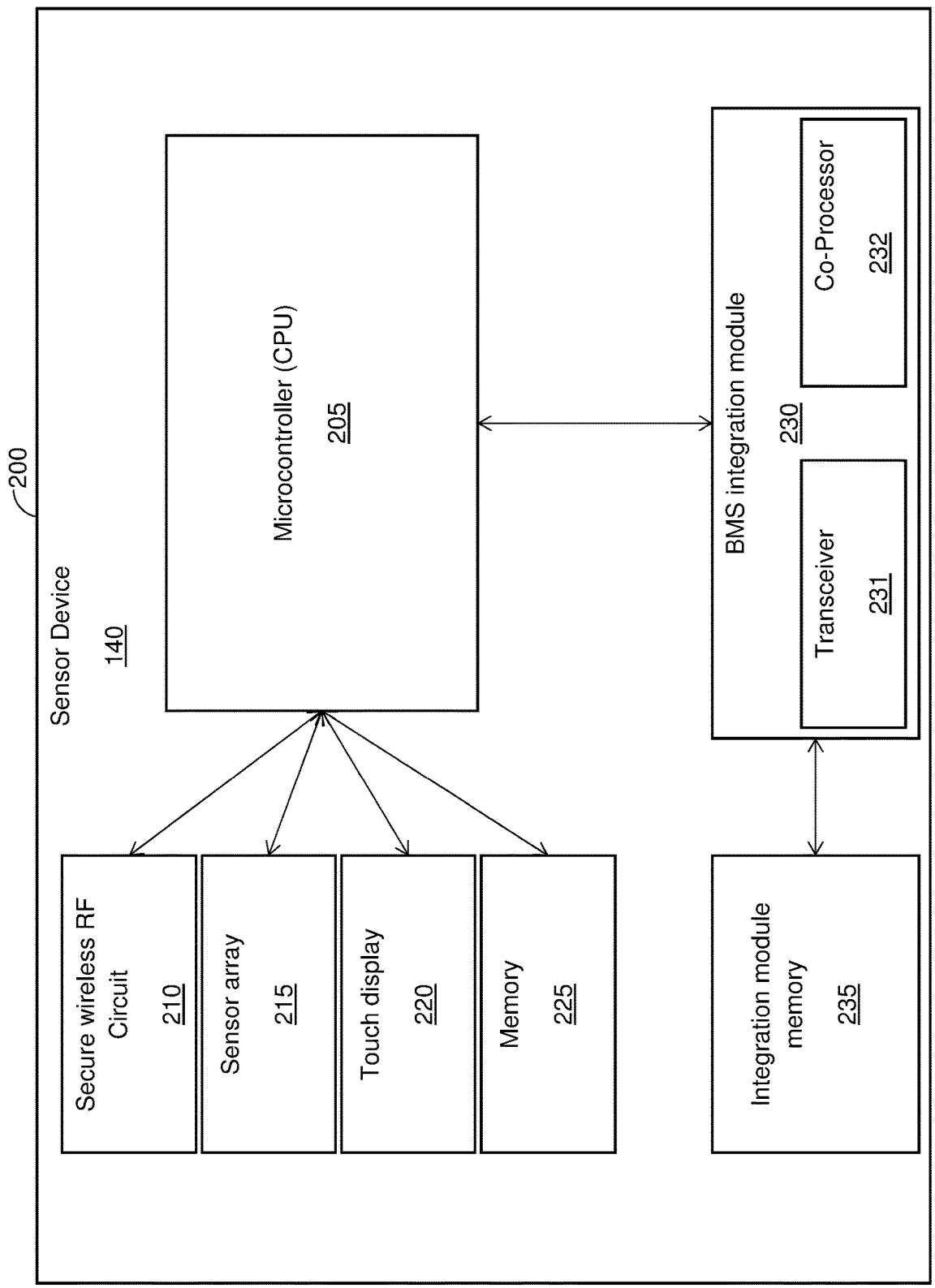
FIG. 2a is a block diagram depicting a sensor device for local management of building air quality assurance, according to an embodiment.

FIG. 2a is an example hardware diagram 200 depicting a sensor device 140 for local management of building air quality assurance, according to an embodiment. The sensor device 140 may include one or more components including, without limitation, a microcontroller 205, a secure wireless radio-frequency (RF) circuit 210, a sensor array 215, a touch display 220, a memory 225, a building management system (BMS) integration module 230, an integration module memory 235, and the like, as well as any combination thereof.

The microcontroller 205 is a processing component configured to execute instructions, organize or process data, perform other, like, processing tasks, and any combination thereof. The microcontroller 205 may be a single physical component, multiple individual components, connected to provide for processing of data as described, and the like. The microcontroller 205 may be configured to execute one or more instructions or other, like, processes pertaining to the methods described hereinbelow. A detailed description of a microcontroller unit 205 is provided with respect to FIG. 2b, below.

A secure wireless RF circuit 210 is configured to provide for radio-frequency communication between the sensor device 140 and the various components of the network, such as the network described with respect to FIG. 1, above. Specifically, the secure wireless RF circuit 210 may be configured to receive data, to transmit data, or to receive and transmit data, including simultaneously at least from the bridge device 130. The secure wireless RF circuit 210 may be configured to connect with various components of a wireless system via one or more protocols including, without limitation, industrial, scientific, and medical (ISM)-band radio, Wi-Fi, Bluetooth®, cellular, long-term evolution (LTE), and the like. Data sent and received via the secure wireless RF circuit 210 may be encrypted, unencrypted, or partially-encrypted, and the secure wireless RF circuit 210 may be configured to encrypt or decrypt sent and received data, including to various degrees of encryption. The secure wireless RF circuit 210 may be connected to the microcontroller 205 via one or more means including, without limitation, via a serial peripheral interface (SPI), and the like, as well as any combination thereof.

The secure wireless RF unit 210 may be configured to send and receive data to and from one or more bridge devices, such as the bridge devices, 130, of FIG. 1, above, according to the means described herein. The secure wireless RF circuit 210 may be configured to receive data from a bridge device, where such data may include, as examples and without limitation, data register values, sensor calibration coefficients, sensor user offsets, building management system (BMS) task configurations, firmware images, including operating screens and scripts, as well as custom logo graphics, compiled operating system scripts, and the like, as well as any combination thereof.

Further, in an embodiment, transmissions from the secure wireless RF circuit 210 may be secured by application of one or more encryption methods, algorithms, and the like, to packets, signals, and the like, as well as any combination thereof, transmitted by the secure wireless RF circuit 210. Encryption methods, algorithms, and the like, applied to various packets and signals as described, may be executed by application code running in a device microcontroller 205, providing for encryption and securing the transmission. Further, such application of encryption methods, algorithms, and the like, may provide for insulation of the platform against side-channel attacks directed to sniffing of packets, signals, and the like, moving across an SPI bus. Where one or more data features are received from a bridge device 130 via the secure wireless RF circuit 210, the sensor device 140 may be configured to selectively store and process the received data features.

The sensor array 215 is an environmental data collection component. The sensor array may include one or more environmental data sensor components relevant to collection of building air quality data. Environmental data sensor components which may be included in a sensor array 215 include, as examples and without limitation, carbon dioxide ($CO_2$) sensors, particulate matter sensors, including multiple particulate matter sensors relevant to particulates of various sizes, formaldehyde ($CH_2O$) sensors, carbon monoxide (CO) sensors, temperature sensors, relative humidity sensors, ozone ($O_3$) sensors, wide-band total volatile organic compound (TVOC) sensors, light level sensors, TVOC sensors, and the like, as well as any combination thereof. One or more of the environmental data sensor components included in the sensor array may be configured to provide for collection of building environmental data, such as via the processes described hereinbelow. The sensor array 215 may be connected to the microcontroller 205 via one or more means including, without limitation, SPI connections, and the like, as well as any combination thereof.

The touch display 220 is a user-accessible display and input component. The touch display 220 may be configured to display one or more data features relevant to the operation of the sensor device 140 including, without limitation, custom graphics, environmental data readings, sensor device 140 information, such as calibration settings, firmware versions, and the like, as well as other, like, data features, and any combination thereof. The touch display 220 may be further configured to collect one or more user inputs. A user input may be a user interaction with the touch display 220 including, as examples and without limitation, taps, swipes, holds, scrolls, and the like, as well as any combination thereof. The touch display 220 may be configured to connect with the microcontroller 205 via one or more means including, as examples and without limitation, via SPI connections, and the like, as well as any combination thereof.

The memory 225 is a data storage component configured to provide for storage of one or more data features relevant to the operation of the sensor device 140. The memory 225 may be configured as short-term memory, long-term memory, other, like, memory formats, and any combination thereof. The memory 225 may be volatile (e.g., random access memory, etc.), non-volatile (e.g., read only memory, flash memory, etc.), or a combination thereof. The memory may be further configured to connect with the microcontroller 205 via one or more means including, without limitation, via SPI connections, and the like, as well as any combination thereof.

The BMS integration module 230 is a component configured to provide for integration of the sensor device 140 with one or more building management systems (BMSs). BMSs may be systems included in a building, providing for monitoring of environmental data, control of building environmental management devices, such as air flow regulators, heating furnaces, and the like, as well as monitoring and control of building systems, including simultaneously. The BMS integration module 230 may be configured to connect to the microcontroller 205 via one or more means including, without limitation, via SPI connections, and the like, as well as any combination thereof. The BMS integration module 230 may be configured to include one or more sub-components including, without limitation, a transceiver 231, a co-processor 232, and the like, as well as any combination thereof.

The transceiver 231 of the BMS integration module 230 is a sub-component providing for connection of the BMS integration module 230 with various BMSs and or BMS protocol-enabled devices. The transceiver 231 may be configured to collect data from a BMS and or device, to transmit data to a BMS and or device, or to both collect and transmit data, including simultaneously. The transceiver 231 may be configured to communicate with one or more BMSs, other, similar devices, and the like, as well as any combination thereof, via BMS protocols including, without limitation, BACNet MSTP, Modbus RTU, and the like, as well as any combination thereof by one or more means including, without limitation, RS-based connections (e.g., RS485 communication standard), and the like, as well as any combination thereof. Further, in an embodiment, the transceiver 231 may be configured as an ethernet transceiver, providing for communication via one or more protocols including, without limitation, BACNet IP and MSTP, Modbus TCP and RTU, and the like, as well as any combination thereof.

The co-processor 232 of the BMS integration module 230 is a sub-component providing for processing of BMS data pertinent to and or from the sensor device 140. The co-processor 232 may be configured to provide processing for purposes including, without limitation, formatting of sensor device 140 data and instructions for transmission to BMS devices and systems, formatting of received BMS device and systems data and instructions for respective processing and execution by the sensor device 140, processing and execution of transceiver instructions, and the like, as well as any combination thereof.

The integration module memory 235 is a memory module configured to provide storage for the operation of the BMS integration module 230. The integration module memory 235 may be configured as electronically erasable programmable read-only memory (EEPROM). The integration module memory 235 may be configured to store data temporarily, permanently, or semi-permanently. The memory 225 may be volatile (e.g., random access memory, etc.), non-volatile (e.g., read only memory, flash memory, etc.), or a combination thereof. The integration module memory 235 may be configured to connect with the BMS integration module 230 via one or more means including, without limitation, via SPI connections, and the like, as well as any combination thereof. In an embodiment, the integration module memory 235 may be included in the BMS integration module 230.

Figure 2B:
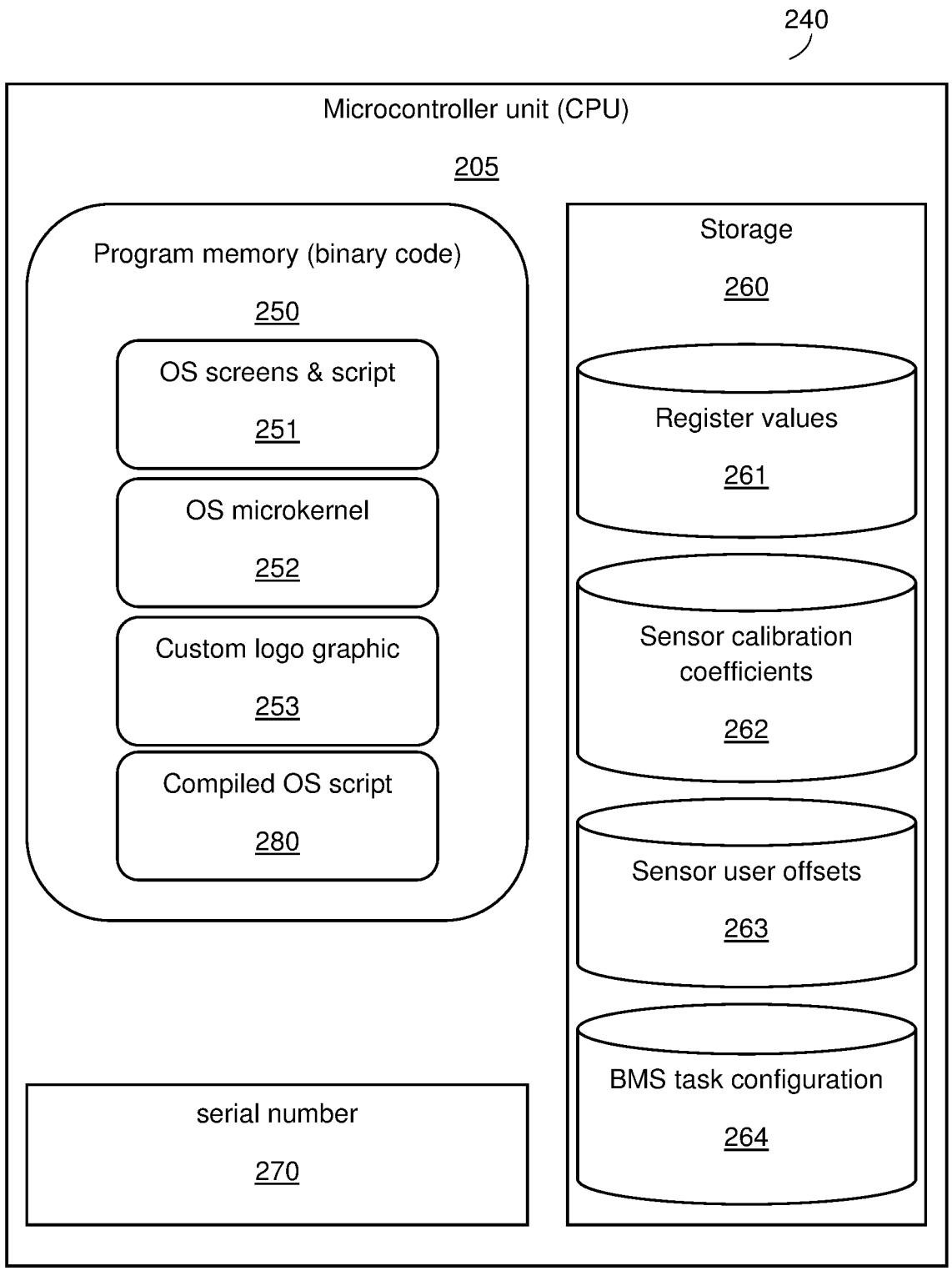
FIG. 2b is a block diagram depicting a microcontroller unit for a sensor device for local management of building air quality assurance, according to an embodiment.

FIG. 2b is a block diagram 240 depicting a microcontroller unit 205 for a sensor device for local management of building air quality assurance, according to an embodiment. The microcontroller unit 205 may include one or more components including, without limitation, a program memory 250, a storage 260, a serial number 270, a compiled operating system script 280, and the like, as well as any combination thereof. The various components included in the microcontroller 205 may be realized as physical components, virtualized components, and various combinations thereof.

The program memory 250 is a memory component including one or more binary code data features. The program memory 250 may be configured to store, temporarily, permanently, or semi-permanently, data related to various processing applications, as may be applicable to the microcontroller unit 205. The program memory 250 may include data features, in binary code format, including, as examples and without limitation, operating system (OS) screens and scripts 251, pertaining to operating system display and functionality, an OS microkernel 252, relevant to execution of personalized code customizations, custom logo graphics 253, as may be provided by users, manufacturers, system administrators, compiled OS scripts 280, as described hereinbelow, and the like, as well as other, like, data features and any combination thereof.

The compiled OS script 280 includes one or more instructions, commands, or other, like, directions configured to execute one or more functions through the microcontroller unit 280. The instructions, commands, or other, like, directions included in the compiled OS script 280 may include instructions and the like relevant to sensor device operating system initialization, modification, and execution, and the like, as well as any combination thereof. Further, in an embodiment, the compiled OS script 280 may be stored in a non-volatile fashion in one or more storage components including, without limitation, the storage 260, and the like, as well as any combination thereof. In an additional embodiment, one or more methods or processes may be applied to execute a compiled OS script 280 via a radio frequency (RF) over-the-air (OTA) transaction.

The storage 260 is a data storage component configured to warehouse, archive, or otherwise store data relevant to the operation of the microcontroller unit 205. The storage 260 may include storage portions relevant to storage of register values 261, as may be applicable to sensor device operations, storage of sensor calibration coefficients 262, as may be relevant to calibration of sensors included in the sensor device 140, storage of sensor user offsets 263, as may be relevant to the various sensors described above, storage of building management system task (BMS) configurations 264, as may be applicable to BMS integration, as well as other, like, storage portions, as well as any combination thereof.

The serial number 270 is a serial number providing for unique identification of a sensor device 140. The serial number 270 may be a 32-bit data feature, or a component providing storage for such a feature, where the memory device containing the serial number may be configured to include encoded descriptions of, as examples and without limitation, manufacturing date, manufacturing location, lot number, batch number, and the like, as well as any combination thereof. In an embodiment, the attributes of the serial number 270 may be re-writeable, providing for modification of the serial number 270 of the sensor device 140.

Figure 3:
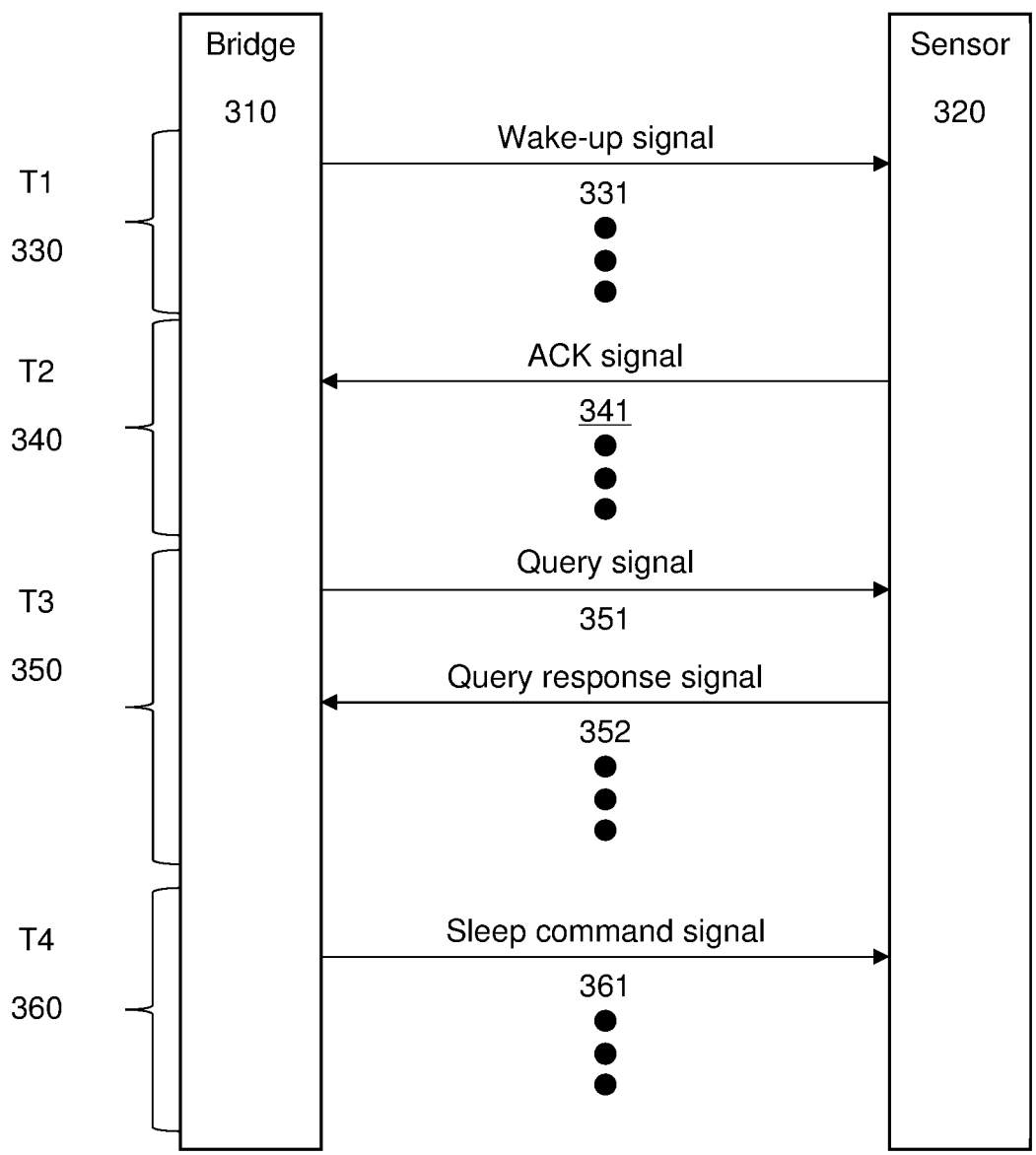
FIG. 3 is an illustration describing an air quality communication protocol, according to an embodiment.

FIG. 3 is an example flow diagram 300 describing the operation an air quality communication protocol, according to an embodiment. An air quality communication protocol may be a protocol configured to provide for secure wireless exchanges of data between one or more components of a system for management of air quality assurance, and the like, including, without limitation, a bridge device 130 and one or more sensor device 140. The protocol may include four distinct time periods, a first time period (T1) 330, a second time period (T2) 340, a third time period (T3) 350, and a fourth time period (T4) 370, as well as other like periods and any combination thereof. The various time periods may be configured to include one or more exchanges of data between bridge 310 and sensor 140 devices, as well as other, like, devices.

Although only one sensor device is depicted in the illustration 300, it may be understood that the embodiments disclosed herein may be applicable to multiple sensor devices connected to the same bridge device without loss of generality or departure from the scope of the disclosure. The bridge device 130 and various connected sensor devices 140 may be configured to operate at one or more pre-defined radio-frequency (RF) channels, providing for separation of communications between various "clusters" of sensor devices 140 connected to separate bridge devices 310.

In an embodiment, the sensor device 140 and bridge device 130 may be configured to switch to a second, separate RF channel at various points within a data exchange protocol, as described herein. Further, in an additional embodiment, bridge devices 310 may be configured to operate on a third, separate RF channel, providing for one-to-one asynchronous communication between bridge device 130 and sensor device 140.

During the first time period (T1) 330, sensor devices 140 receive wake-up signals 331 from a bridge device 130. Wake-up signals 331 may be identical and may be serially-numbered, with the various signal numbers corresponding with an order in which the signals are dispatched. Wake-up signals 331 may be sent from a bridge device 130 at regular time intervals during the first time period 330, including time intervals equal to the length of the first time period 330 divided by the number of wake-up signals 331. As an example, where the length of the first time block 330 is equal to six seconds, and where a total of 600 wake-up signals 331 are sent during the first time period 330, one wake-up signal 331 may be sent by the bridge device 130 for the duration of the first time period 330. Further, during the first time period 330, the bridge 130 and sensors 140 may be configured to communicate on a first RF channel, as described hereinabove.

During the first-time block 330, sensor devices 140 may be configured to operate in a low-power or "sleep" state. In a low-power or "sleep" state, sensor devices 140 may be configured to power one or more onboard radio, or similar, components at frequencies configured to provide for receipt of wake-up signals 331. Sensor devices 140 may be configured to power on onboard radio components on various rolling bases, such as, for example and without limitation, in tenth-second increments, whereby a sensor device 140 may power on an onboard radio component for one tenth of a second once every second for the duration of the first time period 330. Sensor devices 140 may be configured to power on on-board radio components according to timing schedules providing for receipt of at least one wake-up signal 331 during the first time period 330. During the first time period 330, the sensor devices 320 and bridge device may be configured to communicate via a first channel, as described hereinabove for purposes including, as described herein, determining whether one or more sensor devices 130 are "listening" and receptive to receipt of wake-up signals 331.

Further, where a sensor device 320 receives a wake-up signal 331 during the first time period 330, the sensor device 320 may be configured to switch from a low-power or "sleep" state into an "awake" or full-power state.

Further, each sensor 320 may include a slot number, where the slot number may be pre-defined, and where each slot number describes a corresponding timeslot. In an embodiment, the slot number of each sensor 320 may be a unique value between zero and 255. The slot number of a sensor 320 may be equal to one or more values included or encoded in a sensor device's unique serial number. In a further embodiment, the slot number of each sensor 320 may be updated manually by one or more means including, without limitation, update through a CCS, a bridge device 130, or the sensor device 140, other, like, means, and any combination thereof.

During the second time period 340, sensor devices 320 may be configured to send, to a bridge device 130, one or more acknowledgement (ACK) signals 341. ACK signals 341 may be signals configured to acknowledge receipt of wake-up signals 331 and to confirm that the sending sensor device 130 is in an "awake" or full-power state. Sensor devices 130 may be configured to send ACK signals 341 at a time, during the second time period 340, equal to the sensor device's 320 assigned slot number, multiplied by a fixed timeslot length. In a further embodiment, the timeslot length may be dynamically conveyed in the wake-up signal, as described hereinabove. ACK signals 341 may include sensor device 320 data describing, with limitation, device serial numbers, device code revision numbers, and the like, as well as any combination thereof. Further, during the second time period 340, the sensor devices and 320 and bridge device 130 may be configured to communicate using a second RF channel, as described hereinabove for purposes including, without limitation, sending ACK signals 341, as described.

During the third time period 350, sensor devices 320 may receive query or queries 351, from the bridge device 130, and may return query response(s) 352 to the same bridge device. A query 351 may include one or more data features including, without limitation, firmware updates, parameter updates, and the like, requests for collected sensor data, requests for sensor status, and the like, other, like, data features, and any combination thereof. Query response 351 may include data features such as, as examples and without limitation, acknowledgements of receipt and application of various updates, requested data features and registers, and the like, as well as any combination thereof. In an embodiment, the response include data readings of one or more sensors or detectors in the sensor array 215. Further, during the third time block 350, the sensor devices and 320 and bridge device 130 may be configured to communicate using a second RF channel, as described hereinabove for purposes including, without limitation, sending and receiving query signals 351 and query response signals 352, as described herein, and the like, as well as any combination thereof.

During the fourth time period 360, the sensor devices 140 may be configured to receive, from the bridge device 130, sleep command signals 361. Sleep command signals 361 may be signals containing instructions which, when executed by the sensor devices 320, configure the sensor devices 320 to enter a low-power or "sleep" state. Further, during the fourth time period 360, sensor devices 320 may be configured to revert to a first communication channel, as described hereinabove, and the bridge device 130 may be configured to switch to a third communication channel, as described hereinabove.

Further, following completion of the fourth time period 360, where sleep command signals 361 have been received by all sensor devices 320, the sensor devices 320 may be configured to switch to a first communication channel, as described hereinabove, and the bridge device 130 may be configured to switch to a third communication channel, as described hereinabove, for purposes including, without limitation, asynchronous exchange of data with one or more other sensor devices. Where a sensor device 320 and a bridge device 130 exchange data asynchronously after the completion of the fourth time period 360, the exchanging sensor device may be configured to switch to the third communication channel to perform the exchange and, subsequently, revert to the first channel.

The air-quality communication protocol is completely secured where data and signals transferred between the sensor device 140 and the bridge device 130 are encrypted. In an embodiment, the encryption is achieved using encryption keys locally stored in the sensor device 140. A key used for encrypting communications during a session (T1 through T4) is selected from a plurality of encryption keys stored in the memory of the sensor device 140.

The disclosed air-quality communication protocol is designed to allow maximization of the distance between the control device and the plurality of sensor devices, while minimizing power consumption by the sensor devices. This is achieved by using the smallest possible bandwidth by adjusting the bandwidth to support the minimum data rate required to accommodate a payload of a data packet within the allotted time of the time slot.

Figure 4A:
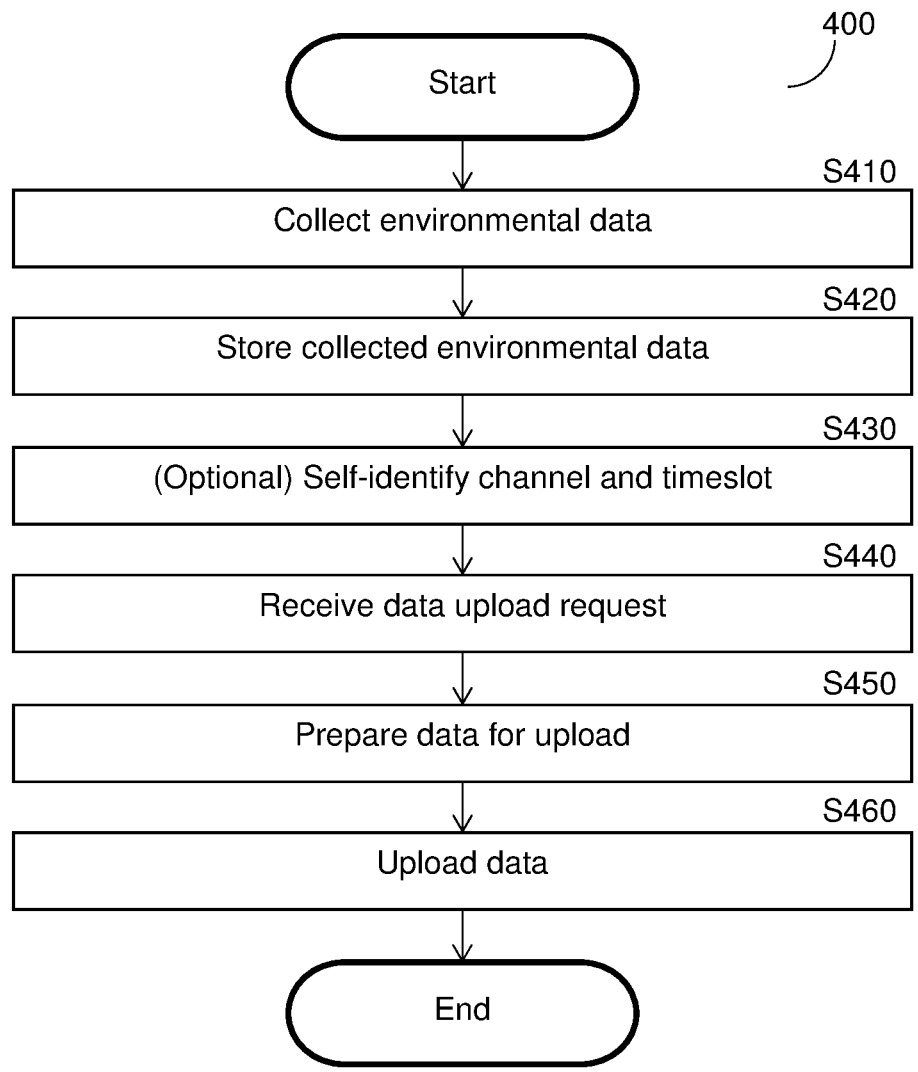
FIG. 4a is a flowchart describing a method for collecting environmental data relevant to local management of building air quality assurance, according to an embodiment.

FIG. 4a is an example flowchart 400 describing a method for collecting environmental data relevant to local management of building air quality assurance, according to an embodiment.

At S410, sensor reading data is collected. Such data relates to building air quality, and the like, as well as any combination thereof. The sensor reading data may include, as examples and without limitation, light levels, temperatures, relative humidity levels, gas and particulate concentrations, and the like, as well as any combination thereof. The collected data may further include metadata including, as examples and without limitation, time and date stamps, sensor device serial numbers, sensor device locations, and the like, as well as any combination thereof. The sensor reading data may be collected from one or more sensor components and detectors, such as those included in the sensor array, 215, of FIG. 2a, above. Collection of sensor reading data is described in detail with respect to FIG. 4b, below. In an embodiment, the sensor reading data relates to the environment's conditions in the area where a sensor device is located.

At S420, the collected send reading data is stored. Collected data may be stored in one or more memory or storage components of the sensor device, 140, of FIG. 2a, above, including, without limitation, the various memory components thereof, the various memory or storage components included in the microcontroller, 205, also of FIG. 2a, above, and the like, as well as any combination thereof. The collected data may be stored in one or more formats including, as examples and without limitation, raw data, as captured by the various sensor components, tables, graphs, charts, machine-interpretable formats, such as comma-separated values (CSV), in other, like, formats, as well as any combination thereof. Environmental data may be stored as encrypted data, unencrypted data, or partially-encrypted data. Further, stored environmental data may be compressed to various degrees.

At the optional S430, the sensor device self-identifies a communication channel and timeslot within a network system. Identification of communication channels and timeslots may provide for bridge-sensor synchronization during a data collection process, such as the data collection process described with respect to the protocol depicted in FIG. 3 Communication channel and timeslot identification may include, without limitation, a bridge device polling phase, wherein a data collection cycle is initiated by pre-determined schedule, conditionally initiated, or by a CCS request, a sensor serial number collection phase, a sensor serial number ordering phase, a collection period length determination phase, wherein a collection period is a period of time describing the length of a sensor device data collection process, a device timeslot identification phase, wherein a device timeslot refers to a sensor device's unique data collection period within the overall data collection period, a communication channel set phase, wherein a communication channel is a low-to-no interference channel providing for transmission of collected sensor data, and the like, as well as any combination thereof.

It may be understood that S430 may be executed at any point prior to execution of S440, including concurrently with S410 or S420, without loss of generality or departure from the scope of the disclosure.

At S440, a data upload request or query is received from a control device. A data upload query specifying upload of data collected and stored at S420. In a typical embodiment, the query may be received from the bridge device. In other embodiments, such query may be received, without limitation, a CCS (e.g., the CCS 110, FIG. 1), the DUS (e.g., DUS 115, FIG. 1), or any software or equipment connected to the sensor device over a network (e.g., the network 110, FIG. 1). A data upload query may be a general request, specifying upload of all stored data. Further, a data upload query may be a specific request, specifying selective upload of one or more data features based on various factors including, without limitation, time or date of collection, collecting sensor type, data matching specific values, and the like. In addition, in an embodiment, a data upload request may specify one or more data upload destinations. Further, in an additional embodiment, a data upload query may specify one or more data upload windows, timeframes, orders, and the like, specifying the timing and manner of data upload.

It may be understood that S440 may be executed at any point prior to the execution of S450, including concurrently with S430, without loss of generality or departure from the scope of the disclosure.

At S450, data is prepared for upload. Data may be prepared for upload by collection of one or more data elements stored at S420. Preparation of data for upload may include conversion of stored data into one or more file types specified in a received request, batching of one or more stored data features, removal of redundant or anomalous data features, and the like, as well as any combination thereof.

At S460, data is uploaded. Data may be uploaded to the one or more destination components included in the received upload request. Uploading data may include transmission of the data prepared at S450 via one or more means including, without limitation, transmission via the secure wireless RF unit, 210, of FIG. 2a, above, transmission via the BMS integration module transceiver, 231, also of FIG. 2a, above, and the like, as well as any combination thereof, including by the means and protocols described with respect thereto. Uploading data at S460 may further include uploading data according to the various schedules, windows, and the like, specified in the received request, providing for upload of collected data according to the specified means and timeframes.

Figure 4B:
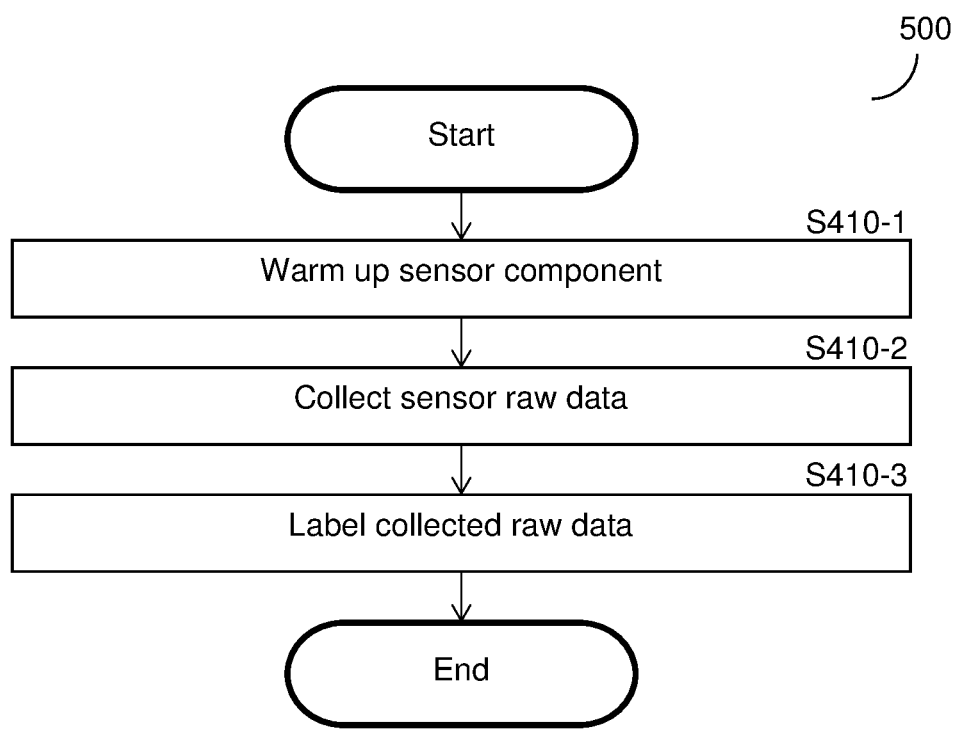
FIG. 4b is a flowchart describing a method for collecting and labeling sensor data to provide analysis-ready environmental data.

FIG. 4b is an example flowchart 500 describing a method for collecting and labeling sensor reading data to provide analysis-ready data. The method described with respect to FIG. 4b may be included as a step of another method described herein, such as, without limitation, S410 of FIG. 3a, above.

At S410-1, a sensor device is warmed up. Warming up a sensor provides for initiation of sensor collection functionality and may be a pre-condition for execution of raw data collection at S410-2. Warming up a sensor may include, without limitation, starting a collection fan or other mechanical component, energizing a membrane or other electrical component, and the like, as well as any combination thereof. Warming up a sensor may be an instantaneous process or may require warm-up time, based on the sensor type. Examples of sensors which may require non-zero warmup times may include, as examples and without limitation, gas concentration sensors, particulate matter concentration sensors, and the like, as well as any combination thereof.

At S410-2, sensor raw data is collected. Raw data may be collected as electrical signal responses from a sensor. Raw data may include, without limitation, voltage data, current data, power data, resistance or resistivity data, and the like, as well as any combination thereof. Sensor raw data may be collected in real-time, based on the observed response of the sensor to environmental conditions. Where a sensor includes a known response lag, the collected raw data may be labeled with the known response lag, as well as other labels, at S410-3.

As an example of raw data collection at S410-3, a light level sensor may be configured to collect ambient light level data based on a measured resistance of a photoresistor. Where the ambient light level in the environment surrounding the sensor remains constant, real-time data reflecting a static value, expressed as a single resistance reading across a given time period, may be collected at S410-3. In the same example, where the ambient light level changes to a higher level, a first static value may be collected reflecting the first light level, and a second static value may be collected reflecting the second light level. In the same example, where multiple light levels are detected, the collected static values may be subsequently labeled at S410-3 to provide for subsequent data analysis.

At S410-3, collected raw data is labeled. Collected raw data may be labeled with one or more data features describing the time, method, and the like, of the collected raw data, features describing conversions of raw data into descriptions of measured values, and the like, as well as any combination thereof. Collected raw data may be labeled with data including times of collection, trends in raw data values, known sensor accuracies, known sensor value collection ranges, such as minima and maxima, known sensor response lags, and the like, as well as any combination thereof. Where collected raw data is labeled with non-zero known sensor response lags, labels describing data features relevant to times of collection, such as histograms and other trends, may be adjusted at S410-3 to include the known sensor response lag.

In an example, where collected raw data includes multiple photoresistor resistance values corresponding to various ambient light levels, the collected raw data may be separated into groups or clusters based on the collected raw data values. The groups or clusters may be subsequently labeled with the times of collection, adjusted to account for the known sensor response lag, providing for identification of time-dependent trends. Further, in the same example, the collected resistance values may be converted into lux values based on a known relationship between collected resistance values and ambient light lux values.

It may be understood that S410-3 may be executed concurrently with S410-2 without loss of generality or departure from the scope of the disclosure.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other sensor units may be connected to the computer platform such as an additional data storage unit and a printing unit. Furthermore, a nontransitory computer readable medium is any computer readable medium except for a transitory propagating signal.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A sensor device operable in an air-quality control system, comprising:
   a radio circuit configured to wirelessly communicate with a control device, wherein the communication is facilitated using an air-quality communication protocol;
   an array of air-quality detectors;
   a processing circuitry; and
   a memory, the memory containing instructions that, when executed by the processing circuitry, configure the sensor device to:
   receive, during a first time period, a wake-up signal, wherein the wake-up signal includes at least a packet number, the wake-up signal being received over a first wireless channel;
   send, during a second time period, an acknowledgment (ACK) signal, wherein the ACK signal is sent in reference to a synchronized time slot and a packet number;
   send, during a third time period, at least sensor reading data of least one air quality detector, wherein the sensor reading data is encrypted using at least an encryption key stored in the memory, wherein the ACK signal and the encrypted sensor reading data are sent over a second wireless channel, and wherein the sleep signal is received over the second channel;
   receive, during a fourth time period, a sleep signal; and
   enter into a sleep mode upon receipt of the sleep signal.

2. The sensor device of claim 1, further comprising after completion of the fourth time period, using a third wireless channel for asynchronous data exchange; and
   upon completion of the asynchronous data exchange, reverting to the first channel.

3. The sensor device of claim 1, wherein the sensor device is configured to listen on the first wireless channel when in the sleep mode.

4. The sensor device of claim 1, wherein the sensor device is further configured to receive calibration commands over the second wireless channel.

5. The sensor device of claim 1, wherein the encryption key is selected from a plurality of encryption keys stored in the memory.

6. The sensor device of claim 1, wherein the radio circuit is configured to communicate over a wireless medium, wherein the wireless medium includes industrial, scientific, and medical (ISM)-band frequency bands.

7. The sensor device of claim 1, wherein the sensor device further comprises:
   a touch screen display configured to display settings of the sensor device and collected sensor readings.

8. The sensor device of claim 1, wherein the array of air-quality detectors includes any one of: a carbon dioxide ($CO_2$) detector, a particulate matter detector, a formaldehyde ($CH_2O$) detector, a carbon monoxide (CO) detector, a relative humidity detector, an ozone ($O_3$) detector, a wide-band total volatile organic compound (TVOC) detector, a light level detector, and a TVOC detector.

9. The sensor device of claim 1, wherein the encrypted sensor reading data is sent in response to a query received from the control device.

10. The sensor device of claim 1, wherein the sensor reading data includes any one of: instantaneous detector readings and past stored detector readings.

11. The sensor device of claim 1, wherein the control device is at least a bridge device configured to control a plurality of sensor devices.

12. The sensor device of claim 1, wherein the sensor device further includes:
    a building management system integration module allowing a communication with a building management system, wherein the building management system integration module includes at least a transceiver and a co-processor.

13. The sensor device of claim 1, wherein the air-quality communication protocol allows for maximization of a distance between the control device and the sensor device, while minimizing power consumption by the sensor device.

14. A method for secured and power-efficient communication between a sensor device and a control device operable in an air-quality system, comprising:
- receiving, during a first time period, a wake-up signal, wherein the wake-up signal includes at least a packet number, the wake-up signal being received over a first wireless channel;
- sending, during a second time period, an acknowledgment (ACK) signal, wherein the ACK signal is sent in reference to a synchronized time slot and a packet number;
- sending, during a third time period, at least sensor reading data of at least one air quality detector, wherein the sensor reading data is encrypted using at least an encryption key, wherein the ACK signal and the encrypted sensor reading data are sent over a second wireless channel, and wherein the sleep signal is received over the second channel;
- receiving, during a fourth time period, a sleep signal; and
- entering into a sleep mode upon receipt of the sleep signal.

15. The method of claim 14, wherein entering into a sleep mode further comprises:
configuring the sensor device to listen on the first channel.

16. The method of claim 14, wherein the sensor device is further configured to receive one or more calibration commands over the second wireless channel.

17. The method of claim 14, wherein the encryption key is selected from a plurality of encryption keys stored in a memory.

18. The method of claim 14, each of the first wireless channel and the second wireless channel are within industrial, scientific, and medical (ISM)-band frequency bands.

19. The method of claim 14, wherein the encrypted sensor reading data is sent in response to a query received from the control device.

20. The method of claim 14, wherein the sensor reading data includes any one of: instantaneous detector readings and past stored detector readings.

* * * * *